United States Patent [19]

Melker

[11] Patent Number: 4,677,978
[45] Date of Patent: Jul. 7, 1987

[54] EMERGENCY CRICOTHYROTOMY SYSTEM AND CRICOTHYROTOMY KIT

[75] Inventor: Richard J. Melker, Gainesville, Fla.

[73] Assignee: University of Florida, Gainesville, Fla.

[21] Appl. No.: 655,317

[22] Filed: Sep. 27, 1984

Related U.S. Application Data

[63] Continuation of Ser. No. 414,680, Sep. 3, 1982, abandoned.

[51] Int. Cl.⁴ .......................................... A61M 16/00
[52] U.S. Cl. ................................ 128/207.14; 128/343; 604/51
[58] Field of Search .............. 128/3, 305, 343, 200.26, 128/207.14, 207.15, 207.16, 207.17; 604/164–170, 51–53

[56] References Cited

U.S. PATENT DOCUMENTS

| | | |
|---|---|---|
| 2,786,469 | 3/1957 | Cohen . |
| 2,873,742 | 2/1959 | Shelden . |
| 2,991,787 | 7/1961 | Shelden et al. .................. 128/305.3 |
| 3,334,631 | 8/1967 | Stebleton . |
| 3,511,243 | 5/1970 | Toy ................................ 128/305.3 |
| 3,688,773 | 9/1972 | Weiss . |
| 3,704,529 | 12/1972 | Cioppa ............................. 128/305 |
| 3,754,554 | 8/1973 | Felbarg . |
| 3,811,449 | 5/1974 | Graulee et al. ..................... 128/343 |
| 3,941,119 | 3/1976 | Corrales ............................ 128/343 |
| 4,306,562 | 12/1981 | Osborne ............................. 604/164 |
| 4,331,138 | 5/1982 | Jessen ............................ 128/305.3 |
| 4,351,333 | 9/1982 | Lazarus et al. ...................... 604/51 |

OTHER PUBLICATIONS

"Transtracheal Catheter Ventilation; Clinical Experience in 36 Patients", Jacobs et al., Chest, vol. 65, pp. 36–40, Jan. 1974.
"A Percutaneous Tracheostomy Device", Toy et al., Surgery, vol. 65, No. 2, pp. 384–389, 1969.

Primary Examiner—C. Fred Rosenbaum
Assistant Examiner—Gene B. Kartchner
Attorney, Agent, or Firm—Kerkam, Stowell, Kondracki & Clarke

[57] ABSTRACT

A method for performing emergency cricothyrotomy ventilation comprising palpating the cricothyroid membrane between the thyroid and cricoid cartilages and thereafter inserting an over-the-needle catheter, needle and syringe into the patient's airway through the incision. Determining that the needle is in the airway by applying gentle back pressure on the plunger of the syringe and, once the catheter, needle and syringe are determined to be in the airway, the needle and the syringe are removed. A guide-wire is fed through the over-the-needle catheter into the airway and, thereafter, the over-the-needle catheter is removed and the cricothyroid membrane is dilated. An air passage catheter is introduced into the dilated membrane along the guide-wire and the guide-wire is thereafter removed and the air passage catheter is secured in its position.

1 Claim, 8 Drawing Figures

EMERGENCY CRICOTHYROTOMY SYSTEM AND CRICOTHYROTOMY KIT

This application is a continuation of application Ser. No. 414,680 filed 9/03/82 which is now abandoned.

TECHNICAL FIELD

The present invention relates to the field of surgical instruments and accessories and to surgical procedures, and more particularly to a method of emergency cricothyrotomy ventilation into the trachea via the cricothyroid membrane.

BACKGROUND OF THE PRIOR ART

A number of devices have been developed for use in securing the airway in emergency situations when endotracheal intubation is not possible. Some devices have been developed for use through the cricothyroid membrane.

One such device and procedure is shown and described in the Jacobs et al. article, *Chest,* Vol. 65, No. 1, January, 1974, pp 36–40, "Transtracheal Catheter Ventilation: Clinical Experience in 36 Patients."

In general, these devices require a skilled surgeon to use properly. Also, many are extremely dangerous. The present device was conceived as an alternative method to safely and quickly securing a patient's airway. The method of introduction of the device was conceived from the inventor's prior experience in placing intravascular catheters by the Seldinger technique. In this technique, the lumen of a vessel is accessed with a needle to obtain blood flow. A guide-wire is then passed down the needle and left in the lumen of the vessel when the needle is revived. A dilator is then placed over the wire into the vessel followed by a sheath of larger size than the original needle. Multiple dilators can be used to allow the introduction of large catheters.

BRIEF SUMMARY OF THE INVENTION

The emergency cricothyrotomy kit of the invention comprises an assembly of surgical instruments used to secure a patent airway in patients with upper airway obstructions or in whom endotracheal intubation is contraindicated or impossible. The emergency cricothyrotomy procedure provides a simple method which allows rapid access to the airway through the cricothyroid membrane.

In general, the assembly of the cricothyrotomy kit comprises a scalpel, an over-the-needle catheter, a syringe adapted to mate with the over-the-needle catheter at the end remote from the needle, a guide-wire having a diameter to be receivable in the hollow needle, a hollow dilator, and on air passage catheter having a diameter receivable about the dilator, and an adapter for immobilizing the airway in the air passage.

Other aspects of the present invention will be apparent to those skilled in the art from the detailed description of the invention in conjunction with the drawings wherein:

FIG. 1 is a top plan view of an assembly or kit of surgical instruments for carrying out the procedure of the present invention; and FIGS. 2 through 8 are diagrammatic views diagrammatically illustrating the procedure of the present invention.

DETAILED DESCRIPTION OF THE INVENTION

Figure 1:
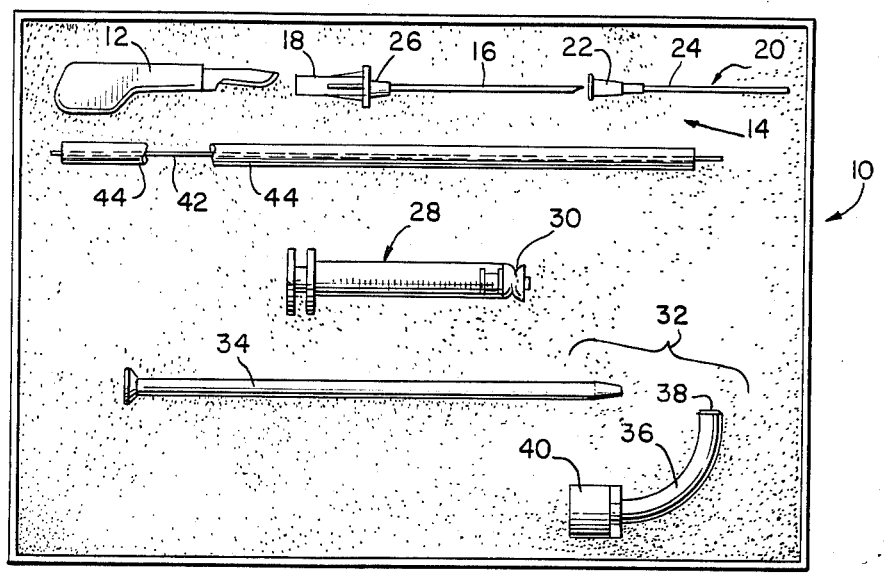
Figure 2:
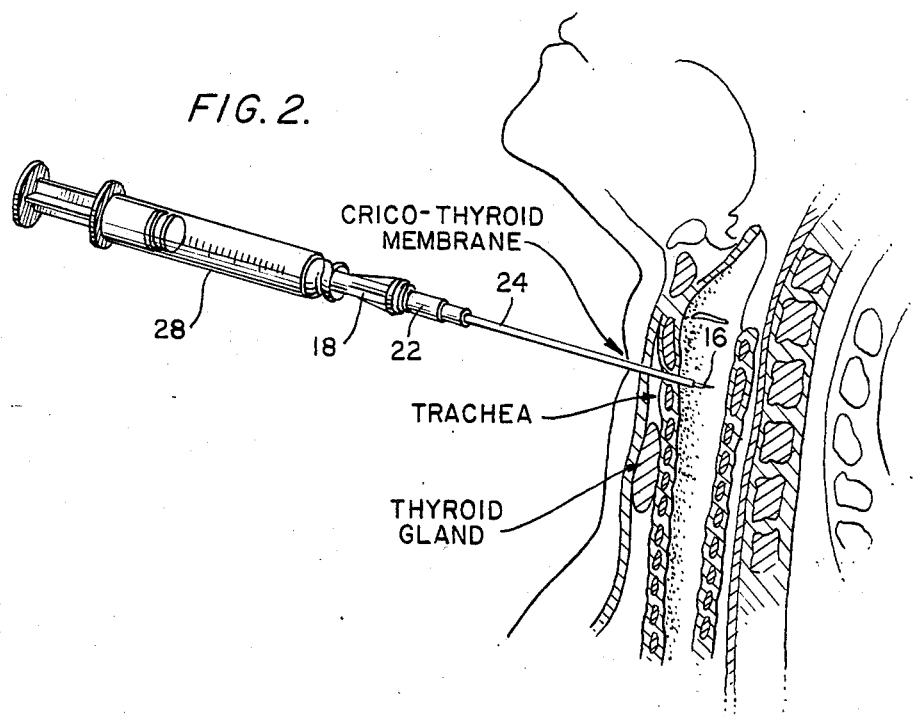
Figure 3:
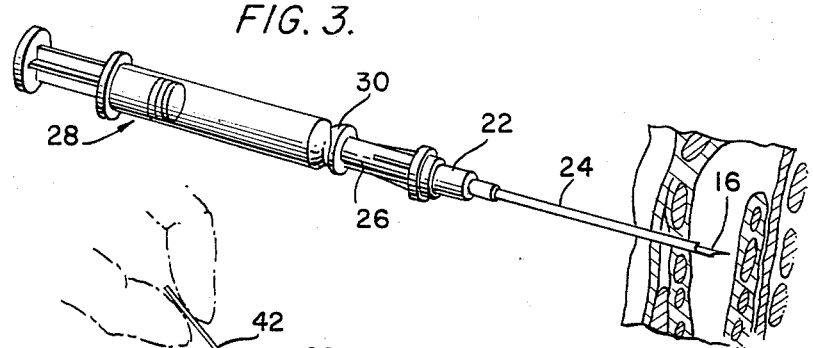

Referring to the drawings and in particular to FIG. 1 thereof, 10 generally designates a container for housing the kit or assembly of the invention. The container 10 houses a scalpel 12 which scalpel may comprise a conventional No. 15 scalpel blade. 14 denotes an over-the-needle catheter including a needle 16 having an adapter end 18. The needle 16 may be a conventional 18 gauge hollow surgical needle. The assembly 14 also includes the catheter portion 20 having an adapter end 22 and a hollow shaft end 24. The internal diameter of the catheter portion is such as to be readily received over the hollow needle 16 and the end portion 22 is sized to snugly receive the adapter portion 26 of the needle assembly.

The kit also includes a syringe 28 having an adapter end 30 which mates with the end of the 18 gauge needle.

The assembly also includes a combination dilator and air passage catheter generally designated 32. The dilator of the assembly 32 denoted 34 has an outside diameter adapted to be received in, for example, 7 centimeter long air passage catheter 36, beveled as at 38 and mated to a standard 15/22 adapter 40.

Figure 5:
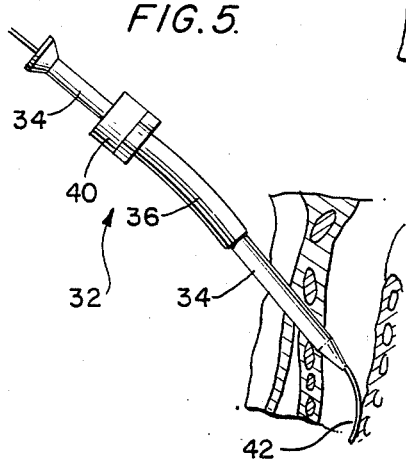

In the preferred embodiment of the invention, the curvature of the air passage catheter 36 is gradual and occurs over the majority of its length. Further, the dilator 34 is preferably manufactured of a stiffer plastic than the air passage catheter 36 so that when the air passage catheter is assembled over the dilator, the air passage catheter is essentially straightened as shown in FIG. 5. When the dilator 34 is removed, FIGS. 6 and 7, the air passage catheter assumes its normal curved configuration in the airway with the distal end pointed down the trachea.

The final element of the kit comprises a guide-wire 42 which is packaged in a protective polyethylene tube 44.

In a preferred mode of the present invention the over-the-needle catheter 20, the air passage catheter 36 and the dilator 34 are made of, for example, polyethylene plastic, and the piston and cylinder of the syringe 28 are made of styrene so that the kit is assembled for a single use and then discarded to provide a single use emergency kit.

In order to introduce the catheter into the cricothyroid membrane for establishing an airway in an emergency situation, the cricothyroid membrane is palpated between the thyroid and cricoid cartilages. The 15 scalpel blade 12 is then used to make an incision through the skin and cricothyroid membrane into the airway.

The 18 gauge over-the-needle catheter 20 as well as the needle 16 and the attached syringe 28 are inserted into the airway through the incision. Gentle back pressure is placed on the plunger of the syringe and air entering the syringe indicates that the catheter is in the airway. The needle 16 and syringe 28 are then removed leaving the plastic catheter 20 in place in the airway.

Figure 4:
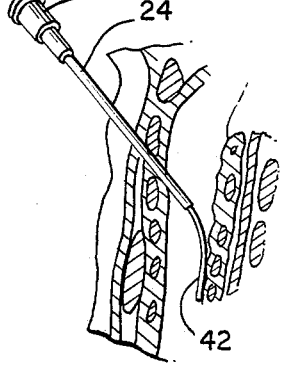

The guide-wire 42 is introduced through the catheter and the catheter 20 is removed (FIG. 4).

Figure 6:
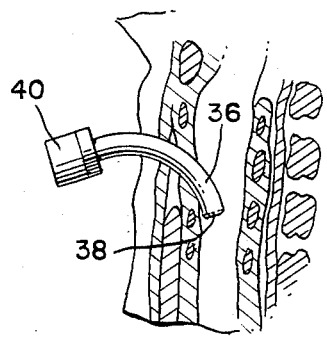
Figure 7:
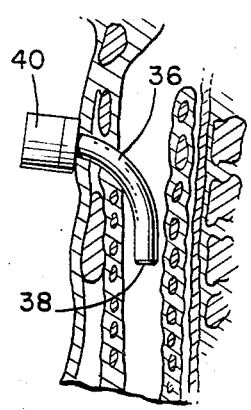
Figure 8:
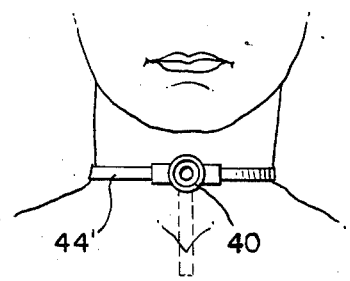

With the guide-wire 42 in the airway, with the air passage catheter in place over the dilator, the cricothyroid membrane is dilated with dilator 34 (FIG. 5). Once the membrane is dilated the air passage catheter 36 is passed into the trachea and the dilator 34 and guide-wire 42 are removed (FIGS. 6 and 7). In FIG. 8, there is illustrated the air passage catheter 36, positioned in the airway of the patient and retained in such position by strap or band 44'. This technique is extremely safe and provides rapid access to the airway in emergency situations.

The internal diameter of a air passage catheter that is placed in the airway is 5.5 mm. Studies using various lengths and diameters of tubing have been performed by the inventor and reveal that tubing 7 cm in length and 5.5 mm in internal diameter allow for adequate oxygenation and ventilation of the average adult with presently available ventilatory support equipment and no special devices. Thus, this device can be used in a variety of situations where emergency access to the airway is necessary without buying any additional support equipment.

Tests have also established that using the 5.5 mm internal diameter air passage catheter, ventilation can be delivered to a victim at tidal volumes and rates recommended by the American Heart Association for cardiopulmonary resuscitation. Unlike the high pressure transtracheal air passage catheter, this catheter allows ventilation with presently available devices and also spontaneous ventilation in a breathing victim. In addition, the present invention allows complete exhalation between inspirations. Many devices similar to the transtracheal catheter provide adequate oxygenation but poor ventilation if the upper airway is obstructed.

I claim:

1. A method for performing emergency cricothyrotomy ventilation permitting spontaneous inspiration and complete exhalation between inspirations comprising the steps:
   palpatating the cricothyroid membrane between the thyroid and cricoid cartilages;
   making an incision in the membrane between the thyroid and cricoid cartilages;
   placing an over-the-needle catheter over a hollow needle;
   inserting an over-the-needle catheter and needle into the airway between the thyroid and cricoid cartilages through the incision with an attached syringe remaining outside of the airway;
   determining that the needle is in the airway by applying gentle back pressure on the syringe;
   removing the needle and syringe;
   feeding a guide-wire through the over-the-needle catheter into the airway;
   removing the over-the-needle catheter;
   dilating the cricothyroid membrane to receive an air passage catheter having an internal diameter of about 5.5 mm thereby permitting spontaneous inspiration and complete exhalation between inspirations;
   introducing an air passage catheter having an internal diameter of about 5.5 mm along the guide-wire into the airway;
   removing the guide-wire and securing the air passage catheter in the airway.

* * * * *